United States Patent
Tsuboike et al.

(10) Patent No.: US 10,801,993 B2
(45) Date of Patent: Oct. 13, 2020

(54) CHEMICAL SENSOR

(71) Applicant: TDK CORPORATION, Tokyo (JP)

(72) Inventors: Sachio Tsuboike, Tokyo (JP); Susumu Haratani, Tokyo (JP); Sumiko Kitagawa, Tokyo (JP); Takashi Kikukawa, Tokyo (JP); Haruki Yuga, Tokyo (JP)

(73) Assignee: TDK CORPORATION, Tokyo (JP)

( * ) Notice: Subject to any disclaimer, the term of this patent is extended or adjusted under 35 U.S.C. 154(b) by 196 days.

(21) Appl. No.: 16/087,833

(22) PCT Filed: Mar. 24, 2017

(86) PCT No.: PCT/JP2017/011936
§ 371 (c)(1),
(2) Date: Sep. 24, 2018

(87) PCT Pub. No.: WO2017/170193
PCT Pub. Date: Oct. 5, 2017

(65) Prior Publication Data
US 2019/0120794 A1    Apr. 25, 2019

(30) Foreign Application Priority Data

Mar. 28, 2016  (JP) .................. 2016-063490

(51) Int. Cl.
*G01N 27/72* (2006.01)
*C12Q 1/6816* (2018.01)
(Continued)

(52) U.S. Cl.
CPC .......... *G01N 27/72* (2013.01); *C12Q 1/6816* (2013.01); *C12Q 1/6825* (2013.01); *G01N 27/745* (2013.01); *G01N 33/54373* (2013.01)

(58) Field of Classification Search
CPC ............... G01N 27/72; G01N 27/745; G01N 33/54373; C12Q 1/6816; C12Q 1/6825
See application file for complete search history.

(56) References Cited

U.S. PATENT DOCUMENTS 8,183,058 B2    5/2012   Hatakeyama et al.
8,283,184 B2 *  10/2012  Ruhrig .................. G01R 33/09
                                                       324/200
(Continued)

FOREIGN PATENT DOCUMENTS

JP    2007-278966 A    10/2007
JP    2008-039782 A    2/2008
(Continued)

OTHER PUBLICATIONS

Jun. 6, 2017 Written Opinion issued in International Patent Application No. PC/JP2017/011936.
Jun. 11, 2020 Office Action issued in U.S. Appl. No. 16/089,122.

*Primary Examiner* — Dennis White
(74) *Attorney, Agent, or Firm* — Oliff PLC

(57) ABSTRACT

A chemical sensor that enables high detection accuracy that includes a soft-magnetic-material film, a magnetoresistance-effect element, a first film disposed over the soft-magnetic-material film, and a second film disposed over the magnetoresistance-effect element, wherein, when viewed from a direction perpendicular to the film surface of the soft-magnetic-material film, the soft-magnetic-material film is disposed at least partially so as not to overlap the magnetoresistance-effect element; when viewed from the direction perpendicular to the film surface of the soft-magnetic-material film, the magnetoresistance-effect element is disposed at least partially so as not to overlap the soft-magnetic-material film; and the second film has higher solubility in a specific liquid than the first film.

19 Claims, 7 Drawing Sheets

(51) Int. Cl.
    *G01N 27/74*     (2006.01)
    *C12Q 1/6825*     (2018.01)
    *G01N 33/543*     (2006.01)

(56) References Cited

U.S. PATENT DOCUMENTS

| | | |
|---|---|---|
| 2005/0087000 A1 | 4/2005 | Coehoorn et al. |
| 2007/0237673 A1 | 10/2007 | Ikeda et al. |
| 2008/0032423 A1 | 2/2008 | Wang et al. |
| 2009/0243594 A1 | 10/2009 | Kahlman |
| 2010/0167263 A1 | 7/2010 | Groll et al. |
| 2011/0156702 A1 | 6/2011 | Kim et al. |
| 2012/0289419 A1 | 11/2012 | Hu et al. |
| 2015/0044778 A1 | 2/2015 | Wang et al. |
| 2018/0299407 A1 | 10/2018 | Haratani et al. |

FOREIGN PATENT DOCUMENTS

| | | |
|---|---|---|
| JP | 2008-525789 A | 7/2008 |
| JP | 2009-002838 A | 1/2009 |
| JP | 2014-506999 A | 3/2014 |
| JP | 2014-528071 A | 10/2014 |
| WO | 2017/082227 A1 | 5/2017 |

\* cited by examiner

CHEMICAL SENSOR

TECHNICAL FIELD

The present disclosure relates to a chemical sensor for detecting a detection target substance in a sample.

BACKGROUND ART

In these years, in order to identify, prevent, or diagnose disease, development has been underway for devices (biosensors) of determining the concentration of or the presence or absence of a biomarker in a sample, such as a protein, a bacterium, a virus, or a nucleic acid (for example, refer to Patent Literature 1).

The applicant has proposed, in Japanese Patent Application No. 2015-220728, as a biosensor for detecting a biomolecule in a sample, as illustrated in a sectional view in FIG. 14, a biosensor $100x$ including a magnetoresistance-effect element $3x$, a soft-magnetic-material thin film $2x$ disposed adjacent to the magnetoresistance-effect element $3x$, and a protective film $4x$ covering the surface of the soft-magnetic-material thin film $2x$, wherein the protective film $4x$ has an outer surface including an affinity substance that recognizes a detection target substance. In the same application, the applicant has also proposed, as a method for detecting a biomolecule with such a biosensor including a magnetoresistance-effect element, a detection method including a step of accumulating, over a protective film, biomolecules in a sample via an affinity substance; a step of accumulating, over the protective film, magnetic beads via the biomolecules; and a step of applying a magnetic field in a direction intersecting with a soft-magnetic-material thin film, to apply a detection magnetic field to the magnetoresistance-effect element, to determine the resistance of the magnetoresistance-effect element. In this case, the resistance of the magnetoresistance-effect element correlates with the number of magnetic beads accumulated over the protective film, which enables determination of the number of biomolecules in the sample.

CITATION LIST

Patent Literature

PTL 1: Japanese Unexamined Patent Application Publication (Translation of PCT Application) No. 2014-506999

SUMMARY

The inventors have found the following problem: in detection of biomolecules (detection target substance) using the above-described biosensor (chemical sensor), even among cases where the number of magnetic beads accumulated over the protective film is the same, the resistance of the magnetoresistance-effect element varies depending on the arrangement of magnetic beads over the protective film, and high detection accuracy is not provided. More specifically, the resistance (or variation in the resistance) of the magnetoresistance-effect element upon disposition of a single magnetic bead over the magnetoresistance-effect element is different from the resistance (or variation in the resistance) of the magnetoresistance-effect element upon disposition of a single magnetic bead over the soft-magnetic-material thin film. As a result, among cases where magnetic beads are disposed over the magnetoresistance-effect element and over the soft-magnetic-material thin film, in spite of the same number of magnetic beads accumulated over the protective film, the resistance of the magnetoresistance-effect element varies depending on the arrangement of the magnetic beads, so that high detection accuracy is not provided, which the inventors found problematic. An object of the present disclosure is to provide a chemical sensor that enables high detection accuracy.

In order to achieve the above-described object, it is desirable to provide a chemical sensor including a soft-magnetic-material film; a magnetoresistance-effect element; a first film disposed over the soft-magnetic-material film; and a second film disposed over the magnetoresistance-effect element, wherein, when viewed from a direction perpendicular to a film surface of the soft-magnetic-material film, the soft-magnetic-material film is disposed at least partially so as not to overlap the magnetoresistance-effect element; when viewed from the direction perpendicular to the film surface of the soft-magnetic-material film, the magnetoresistance-effect element is disposed at least partially so as not to overlap the soft-magnetic-material film; and the second film has higher solubility in a specific liquid than the first film.

In order to achieve the above-described object, it is desirable to provide another chemical sensor including a soft-magnetic-material film; a magnetoresistance-effect element; a first film disposed over the soft-magnetic-material film; and a second film disposed over the magnetoresistance-effect element, wherein, when viewed from a direction perpendicular to a film surface of the soft-magnetic-material film, the soft-magnetic-material film is disposed at least partially so as not to overlap the magnetoresistance-effect element; when viewed from the direction perpendicular to the film surface of the soft-magnetic-material film, the magnetoresistance-effect element is disposed at least partially so as not to overlap the soft-magnetic-material film; a material of the first film is at least one selected from the group consisting of silicon, titanium, zirconium, indium, tantalum, iron, cobalt, nickel, copper, cadmium, bismuth, gold, silver, rhodium, ruthenium, palladium, and alloys of combinations thereof, or an oxide of at least one selected from the group consisting of silicon, titanium, zirconium, indium, tantalum, iron, cobalt, nickel, copper, cadmium, bismuth, and combinations thereof, or at least one selected from the group consisting of carbon, diamond-like carbon, and resin; and a material of the second film is at least one selected from the group consisting of aluminum, zinc, gallium, tin, lead, niobium, molybdenum, tungsten, and alloys of combinations thereof, or an oxide of at least one selected from the group consisting of aluminum, zinc, gallium, tin, lead, niobium, molybdenum, tungsten, and combinations thereof.

In order to achieve the above-described object, it is desirable to provide another chemical sensor including a soft-magnetic-material film; a magnetoresistance-effect element; a first film disposed over the soft-magnetic-material film; and a second film disposed over the magnetoresistance-effect element, wherein, when viewed from a direction perpendicular to a film surface of the soft-magnetic-material film, the soft-magnetic-material film is disposed at least partially so as not to overlap the magnetoresistance-effect element; when viewed from the direction perpendicular to the film surface of the soft-magnetic-material film, the magnetoresistance-effect element is disposed at least partially so as not to overlap the soft-magnetic-material film; a material of the first film is at least one selected from the group consisting of silicon, titanium, zirconium, indium, tantalum, niobium, molybdenum, tungsten, gold, silver, rhodium, ruthenium, palladium, and alloys of combinations thereof, or an oxide of at least one selected from the group consisting of silicon, titanium, zirconium, indium, tantalum, niobium, molybdenum, tungsten, and combinations thereof, or at least one selected from the group consisting of carbon, diamond-like carbon, and resin; and a material of the second film is at least one selected from the group consisting of aluminum, zinc, gallium, tin, lead, iron, cobalt, nickel, copper, cadmium, bismuth, and alloys of combinations thereof, or an oxide of at least one selected from the group consisting of aluminum, zinc, gallium, tin, lead, iron, cobalt, nickel, copper, cadmium, bismuth, and combinations thereof.

DESCRIPTION OF EMBODIMENTS

Preferred embodiments for working the present disclosure will be described in detail with reference to the drawings. The descriptions of the embodiments below do not limit the present invention. Constituent features described below encompass features that those skilled in the art readily conceive, and features that are substantially the same as or equivalent to the constituent features. Such constituent features described below can be appropriately combined. Such constituent features can be omitted, substituted, or modified in various ways without departing from the spirit and scope of the present disclosure.

<Basic Configuration of Chemical Sensor>

Figure 1:
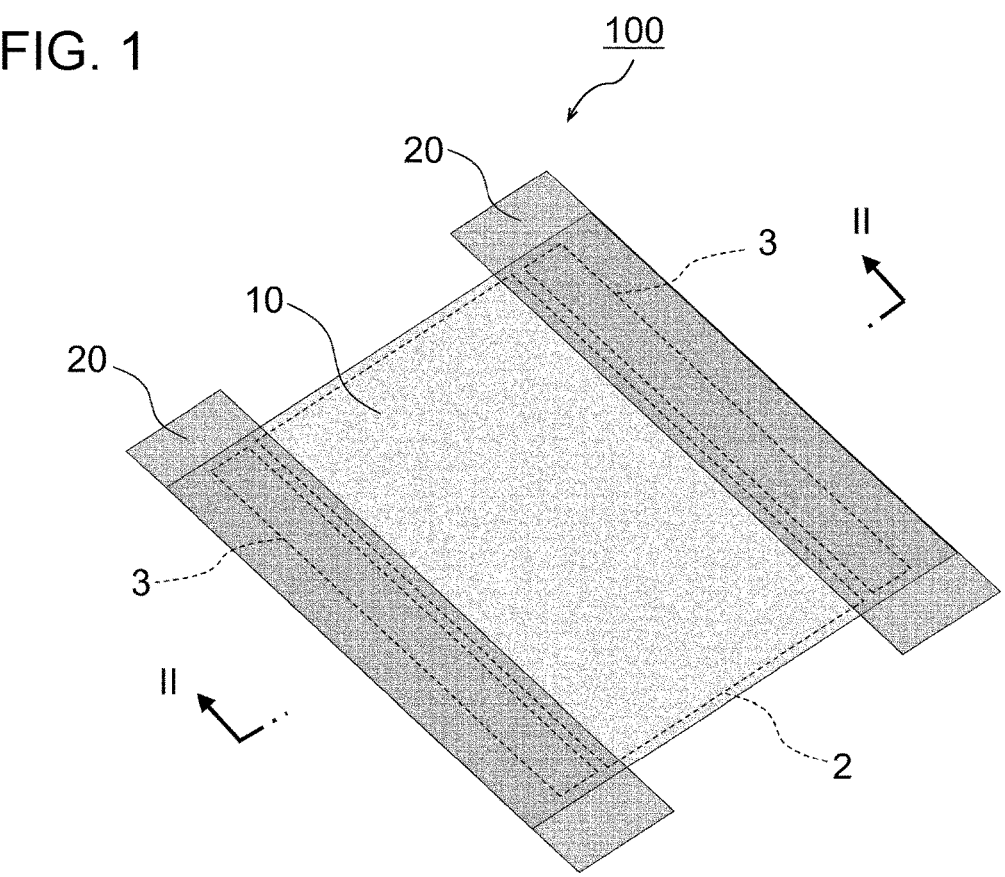
FIG. 1 is a perspective view of a chemical sensor according to a first embodiment.
Figure 2:
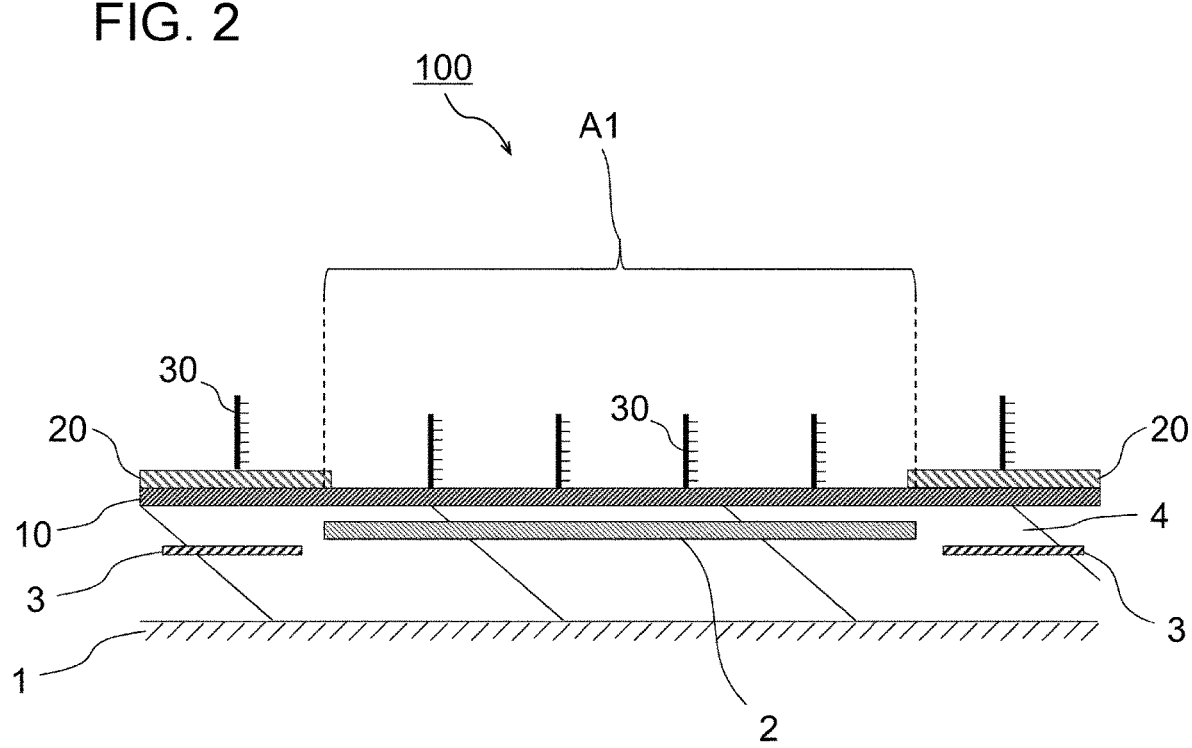
FIG. 2 is a sectional view of the chemical sensor according to the first embodiment, taken along line II-II in FIG. 1.

FIG. 1 is a perspective view of a main portion of a chemical sensor 100 according to a first embodiment. FIG. 2 is a sectional view taken along line II-II in FIG. 1. The chemical sensor 100 detects a detection target substance 40 in a sample. The chemical sensor 100 includes, over a substrate 1, a soft-magnetic-material film 2, a magnetoresistance-effect element 3, a first film 10 disposed over the soft-magnetic-material film 2, and a second film 20 disposed over the magnetoresistance-effect element 3. When viewed from a direction perpendicular to the film surface of the soft-magnetic-material film 2, the soft-magnetic-material film 2 is disposed at least partially so as not to overlap the magnetoresistance-effect element 3. When viewed from the direction perpendicular to the film surface of the soft-magnetic-material film 2, the magnetoresistance-effect element 3 is disposed at least partially so as not to overlap the soft-magnetic-material film 2. The chemical sensor 100 further includes a protective film 4 covering a surface of the substrate 1, and surrounding the soft-magnetic-material film 2 and the magnetoresistance-effect element 3. The first film 10 has a surface having a first region A1 facing the soft-magnetic-material film 2, and has, in the first region A1, an organic material including an affinity substance (capture probe 30) that binds to a detection target substance 40. The first film is a film where the detection target substance 40 is accumulated over the first region A1. The second film 20 has higher solubility in a specific liquid (dissolving liquid described later) than the first film 10. In the chemical sensor 100 illustrated in FIGS. 1 and 2, two magnetoresistance-effect elements 3 are disposed on both sides of the soft-magnetic-material film 2 in a direction parallel to the film surface of the soft-magnetic-material film 2. As illustrated in FIGS. 1 and 2, the first film 10 is disposed over the soft-magnetic-material film 2 and the magnetoresistance-effect elements 3, and the second film 20 is disposed on the first film 10. Incidentally, in FIG. 2 and FIGS. 3 to 13 described later, the capture probe 30, the detection target substance 40, the magnetic beads 5, a labeling probe 50, a probe 60, and the like are exaggeratedly and schematically illustrated.

<Substrate>

The substrate 1 may be formed of a semiconductor or conductor, such as silicon or AlTiC (AlTiC), or an insulator, such as alumina or glass. The shape of the substrate 1 is not particularly limited.

<Soft-Magnetic-Material Film>

The soft-magnetic-material film 2 has a function of changing the direction of a magnetic field 6 (described later) applied in a direction intersecting with the film surface of the soft-magnetic-material film 2, and the direction of a leakage magnetic field (stray magnetic field) generated from the magnetic beads 5 described later by application of the magnetic field 6, to the direction of the film surface (magnetosensitive direction of the magnetoresistance-effect element 3), to transfer these magnetic fields to the magnetoresistance-effect element 3. The magnetic field 6 applied in the direction intersecting with the film surface of the soft-magnetic-material film 2, and the leakage magnetic field (stray magnetic field) generated from the magnetic beads 5 by application of the magnetic field 6 are directed, by the soft-magnetic-material film 2, in the film-surface direction of the soft-magnetic-material film 2, and are applied from an end surface of the soft-magnetic-material film 2 to the magnetoresistance-effect element 3. The material of the soft-magnetic-material film 2 is, for example, Permalloy.

<Magnetoresistance-Effect Element>

The magnetoresistance-effect element 3 is disposed such that its stacked-layer surface is substantially parallel to the film surface of the soft-magnetic-material film 2. The magnetoresistance-effect element 3 is preferably a spin-valve element including a pinned layer having a magnetization direction pinned in a certain direction in the stacked-layer surface, a free layer having a magnetization direction variable depending on an outer magnetic field, and an intermediate layer positioned between the pinned layer and the free layer. The material of the intermediate layer is a nonmagnetic conductor or insulator. The magnetoresistance-effect element 3 in which the intermediate layer is a conductor is referred to as a GMR (giant magnetoresistance effect) element, while the magnetoresistance-effect element 3 in which the intermediate layer is an insulator is referred to as a TMR (tunneling magnetoresistance effect) element. The resistance of the magnetoresistance-effect element 3 varies depending on the relative angle between the magnetization direction of the pinned layer and the magnetization direction of the free layer.

The pinned direction of the pinned layer is preferably substantially parallel or substantially antiparallel to a magnetic field (hereafter, also referred to as a detection magnetic field) applied from an end surface of the soft-magnetic-material film 2 to the magnetoresistance-effect element 3. In other words, when viewed from a direction perpendicular to the film surface of the soft-magnetic-material film 2, the soft-magnetic-material film 2 and the magnetoresistance-effect element 3 are preferably disposed on the same straight line in the magnetization direction of the pinned layer of the magnetoresistance-effect element 3. Furthermore, in the two magnetoresistance-effect elements 3, preferably, the pinned directions of the pinned layers are substantially in the same direction. Incidentally, in this embodiment, substantially parallel or substantially antiparallel may be roughly parallel or antiparallel, and may be deviated by 10° or less from being parallel or antiparallel.

When viewed from a direction perpendicular to the film surface of the soft-magnetic-material film 2, the magnetoresistance-effect element 3 is disposed at least partially so as not to overlap the soft-magnetic-material film 2. As illustrated in FIG. 2, when viewed from a direction perpendicular to the film surface of the soft-magnetic-material film 2, the whole magnetoresistance-effect element 3 may be disposed so as not to overlap the soft-magnetic-material film 2. Alternatively, when viewed from a direction perpendicular to the film surface of the soft-magnetic-material film 2, the magnetoresistance-effect element 3 may be disposed so as to partially overlap the soft-magnetic-material film 2.

<Protective Film>

The protective film 4 is preferably an insulating film. Examples of the material of the protective film 4 include inorganic substances such as aluminum oxide, aluminum nitride, silicon oxide, and silicon nitride, and organic substances such as polyimide.

<First Film>

When viewed from a direction perpendicular to the film surface of the soft-magnetic-material film 2, the first film 10 is disposed at least over the soft-magnetic-material film 2, which does not overlap the magnetoresistance-effect element 3. The material of the first film 10 has low solubility in a dissolving liquid described later. When the dissolving liquid is an alkaline liquid, the material of the first film 10 is, for example, at least one selected from the group consisting of silicon, titanium, zirconium, indium, tantalum, iron, cobalt, nickel, copper, cadmium, bismuth, gold, silver, rhodium, ruthenium, palladium, and alloys of combinations thereof. When the dissolving liquid is an alkaline liquid, the material of the first film 10 may be an oxide of at least one selected from the group consisting of silicon, titanium, zirconium, indium, tantalum, iron, cobalt, nickel, copper, cadmium, bismuth, and combinations thereof, or at least one selected from the group consisting of carbon, diamond-like carbon, and resin.

When the dissolving liquid is an acidic liquid, the material of the first film 10 is, for example, at least one selected from the group consisting of silicon, titanium, zirconium, indium, tantalum, niobium, molybdenum, tungsten, gold, silver, rhodium, ruthenium, palladium, and alloys of combinations thereof. When the dissolving liquid is an acidic liquid, the material of the first film 10 may be an oxide of at least one selected from the group consisting of silicon, titanium, zirconium, indium, tantalum, niobium, molybdenum, tungsten, and combinations thereof, or at least one selected from the group consisting of carbon, diamond-like carbon, and resin.

<Second Film>

The material of the second film 20 has high solubility in a dissolving liquid described later. When the dissolving liquid is an alkaline liquid, the material of the second film 20 is, for example, at least one selected from the group consisting of aluminum, zinc, gallium, tin, lead, niobium, molybdenum, tungsten, and alloys of combinations thereof. When the dissolving liquid is an alkaline liquid, the material of the second film 20 may be an oxide of at least one selected from the group consisting of aluminum, zinc, gallium, tin, lead, niobium, molybdenum, tungsten, and combinations thereof.

When the dissolving liquid is an acidic liquid, the material of the second film 20 is, for example, at least one selected from the group consisting of aluminum, zinc, gallium, tin, lead, iron, cobalt, nickel, copper, cadmium, bismuth, and alloys of combinations thereof. When the dissolving liquid is an acidic liquid, the material of the second film 20 may be an oxide of at least one selected from the group consisting of aluminum, zinc, gallium, tin, lead, iron, cobalt, nickel, copper, cadmium, bismuth, and combinations thereof.

The solubility of the second film 20 in the dissolving liquid is higher than the solubility of the first film 10 in the dissolving liquid under the same conditions, and is preferably 10 or more times higher than the solubility of the first film 10 in the dissolving liquid under the same conditions.

<Detection Target Substance>

Examples of the detection target substance 40 include proteins such as antigens and antibodies, nucleic acids such as DNA and RNA, cells, viruses, bacteria, and fungi. The detection target substance 40 also encompasses complexes constituted by, for example, some of proteins such as antigens and antibodies, nucleic acids such as DNA and RNA, cells, viruses, bacteria, and fungi.

Alternatively, a complex constituted by a detection target substance and another substance, or a substance transformed from a detection target substance may be employed as the detection target substance 40. For example, RNA serving as a detection target may be hybridized to biotin-terminated DNA, and the resultant complex may be employed as the detection target substance 40. Such a detection target substance 40 provided as a complex labeled with biotin can specifically bind to streptavidin. The detection target substance 40 binds to the capture probe 30 and the magnetic bead 5 (labeling probe 50) described later, and preferably has a site binding to the capture probe 30 and another site binding to the magnetic bead 5 (labeling probe 50).

The sample containing the detection target substance 40 is not particularly limited as long as it contains the detection target substance 40: for example, in the case of using the chemical sensor 100 for diagnosing disease, examples of the sample include blood, lymph, cerebrospinal fluid, semen, saliva, and urine of a subject such as an individual confirmed as having developed disease, an individual suspected to have developed disease, or a patient treated for disease. Such blood, lymph, cerebrospinal fluid, semen, saliva, urine, or the like may be subjected to a pretreatment to provide a sample free of contaminants that adversely affect detection. For example, when a nucleic acid such as DNA or RNA is employed as the detection target substance 40, the nucleic acid is desirably extracted from blood, lymph, cerebrospinal fluid, semen, saliva, urine, or the like to provide, as a sample, a liquid containing the extracted nucleic acid.

<Capture Probe>

The capture probe 30 is an affinity substance that binds to the detection target substance 40. The capture probe 30 preferably specifically (with high selectivity) binds to the detection target substance 40, and is appropriately selected in accordance with the type of detection target substance 40. For example, when the detection target substance 40 is a nucleic acid, the capture probe 30 may be a nucleic acid complementary to the nucleic acid; when the detection target substance 40 is an antigen, the capture probe 30 may be an antibody that binds to the antigen; when the detection target substance 40 is a primary antibody, the capture probe 30 may be an antigen or secondary antibody that binds to the primary antibody; and, when the detection target substance 40 is a cell, a virus, a bacterium, a fungus, or the like, the capture probe 30 may be an antibody that binds to an antigen present on the surface of the cell, the virus, the bacterium, the fungus, or the like.

The capture probe 30 is immobilized, via an organic material referred to as a linker, on the first region A1 of a surface of the first film 10, the first region A1 facing the soft-magnetic-material film 2 (when viewed from a direction perpendicular to the film surface of the soft-magnetic-material film 2, the soft-magnetic-material film 2 does not overlap the magnetoresistance-effect element 3). The linker is appropriately selected in accordance with its bindability to the first film 10. For example, when the first film 10 is an oxide, the linker may be a silane coupling agent, a phosphonic acid derivative, or the like; when the first film 10 is a metal such as gold or silver, the linker may be a thiol derivative, a disulfide derivative, or the like. The linker intramolecularly has a functional group that forms a bond with the capture probe 30. For example, when the capture probe 30 has a carboxy group, a linker intramolecularly having an amino group is employed. Alternatively, when the capture probe 30 has an amino group, a linker intramolecularly having a carboxy group is employed.

Alternatively, the capture probe 30 may be directly immobilized, without the linker, on the first region A1 of the surface of the first film 10. For example, when the capture probe 30 is a thiol-group-terminated nucleic acid and the first film 10 is gold, the capture probe 30 may be directly bound to, without the linker, the first film 10. For example, when the capture probe 30 is an antibody and the first film is resin, physical adsorption may be employed to directly immobilize the capture probe 30 on the first film 10.

<Method for Producing Chemical Sensor>

An example of a method for producing the chemical sensor 100 will be briefly described. The soft-magnetic-material film 2, the magnetoresistance-effect elements 3, the protective film 4, the first film 10, and the second films 20 are formed over the substrate 1 by a vacuum film-formation technique and a photolithographic technique.

Subsequently, for example, a dipping method or a spotting method is used to bring a solution containing a linker dissolved therein into contact with the first film 10 and the second films 20, and the solution is left for a certain period of time. As a result, the linker binds to the surfaces of the first film 10 and the second films 20. The solvent of the solution containing the linker is, for example, ethanol, butanol, or toluene, and is appropriately selected in accordance with the types of the linker, the first film 10, and the second films 20.

Subsequently, for example, a dipping method or a spotting method is used to bring an aqueous solution containing the capture probe 30 dissolved therein into contact with the first film 10 and the second films 20 having the linker on their surfaces, and the aqueous solution is left for a certain period of time. As a result, the capture probe 30 is immobilized, via the linker, on the first film 10 and the second films 20. In this way, the chemical sensor 100 is produced.

<Method for Detecting Detection Target Substance>

Hereinafter, a method for detecting the detection target substance 40 using the chemical sensor 100 will be described. The method for detecting the detection target substance 40 using the chemical sensor 100 includes a detection-target-substance accumulation step of bringing a sample containing the detection target substance 40 into contact with the first film 10 and the second films 20, to accumulate the detection target substance 40 over the first film 10; a magnetic-bead accumulation step of bringing a liquid containing magnetic beads 5 into contact with the first film 10 and the second films 20, to cause the magnetic beads to be accumulated over the first film 10; a dissolution step of bringing a dissolving liquid into contact with the first film 10 and the second films 20 to dissolve the second films 20; and a determination step of applying a magnetic field 6 in a direction intersecting with the soft-magnetic-material film 2, to apply a detection magnetic field to the magnetoresistance-effect elements 3, and determining the resistance of or variation in the resistance of the magnetoresistance-effect elements 3. Hereinafter, these steps will be described in detail.

(Detection-Target-Substance Accumulation Step)

The detection-target-substance accumulation step is a step of bringing a sample containing the detection target substance 40 into contact with the first film 10 and the second films 20, to accumulate the detection target substance 40 over the first film 10. In view of, for example, simplicity, the chemical sensor 100 is preferably used in a microfluidic device. In the detection-target-substance accumulation step, the sample containing the detection target substance 40 is first passed through a microchannel of a microfluidic device, to thereby bring the sample containing the detection target substance 40 into contact with the first film 10 and the second films 20.

Figure 3:
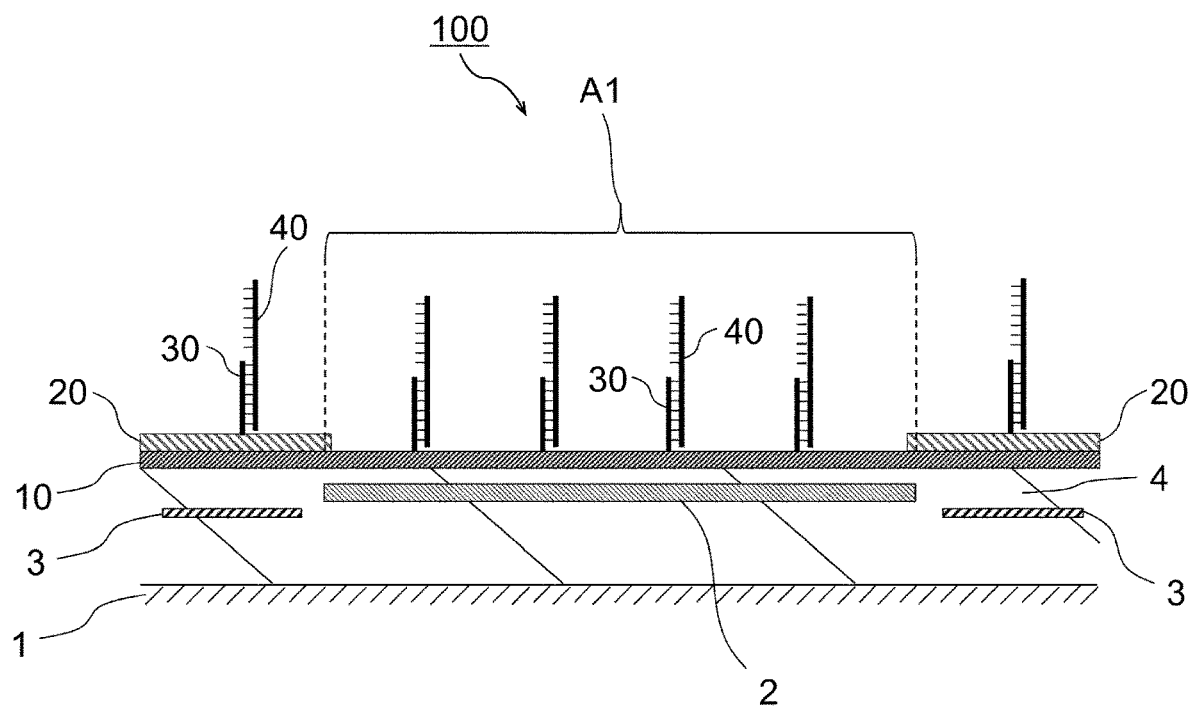
FIG. 3 is a sectional view of the chemical sensor according to the first embodiment after a detection-target-substance accumulation step.

As illustrated in the sectional view in FIG. 3, the detection target substance 40 in the sample flowing through the microchannel binds to the capture probe 30 on the first film 10 and the second films 20. The detection target substance 40 and the capture probe 30 form complexes over the first film 10 and the second films 20 by means of hybridization or an antigen-antibody reaction, for example. After formation of complexes of the capture probe 30 and the detection target substance 40 over the first film 10, the first film 10 and the second films 20 are preferably rinsed with a buffer, for example. Such rinsing enables removal of contaminants that do not form, together with the capture probe 30, complexes, to thereby enhance the detection accuracy for the detection target substance 40.

(Magnetic-Bead Accumulation Step)

The magnetic-bead accumulation step is a step of bringing a liquid containing the magnetic beads 5 into contact with the first film 10 and the second films 20, to accumulate the magnetic beads 5 over the first film 10. In the magnetic-bead accumulation step, the liquid containing the magnetic beads 5 is passed through a microchannel, to thereby bring the liquid containing the magnetic beads 5 into contact with the first film 10 and the second films 20.

Figure 4:
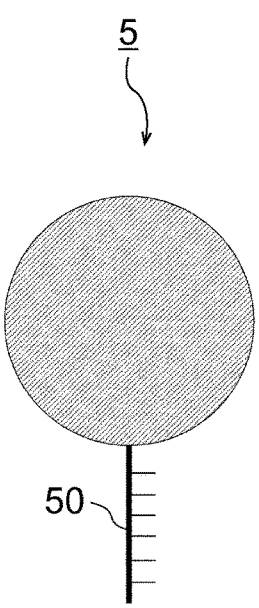
FIG. 4 is a schematic sectional view of a magnetic bead.

The magnetic beads 5 are, for example, beads formed of an organic material and containing magnetic particles therein. More specifically, such beads may be polystyrene beads containing a plurality of iron oxide particles in the core, for example. The iron oxide particles contained in the core are each, for example, a particle having a particle diameter of 100 nm or less and exhibiting superparamagnetism. As illustrated in FIG. 4, such a magnetic bead 5 has, on its surface, an affinity substance (labeling probe 50) that binds to the detection target substance 40. The labeling probe 50 preferably specifically (with high selectivity) binds to the detection target substance 40, and is appropriately selected in accordance with the type of detection target substance 40. For example, when the detection target substance 40 is a nucleic acid, the labeling probe 50 may be a nucleic acid complementary to the nucleic acid; when the detection target substance 40 is an antigen, the labeling probe 50 may be an antibody that binds to the antigen; when the detection target substance 40 is a primary antibody, the labeling probe 50 may be an antigen or secondary antibody that binds to the primary antibody; when the detection target substance 40 is a cell, a virus, a bacterium, a fungus, or the like, the labeling probe 50 may be an antibody that binds to an antigen present on the surface of the cell, the virus, the bacterium, the fungus, or the like; and, when the detection target substance 40 is a substance having biotin, the labeling probe 50 may be streptavidin.

Figure 5:
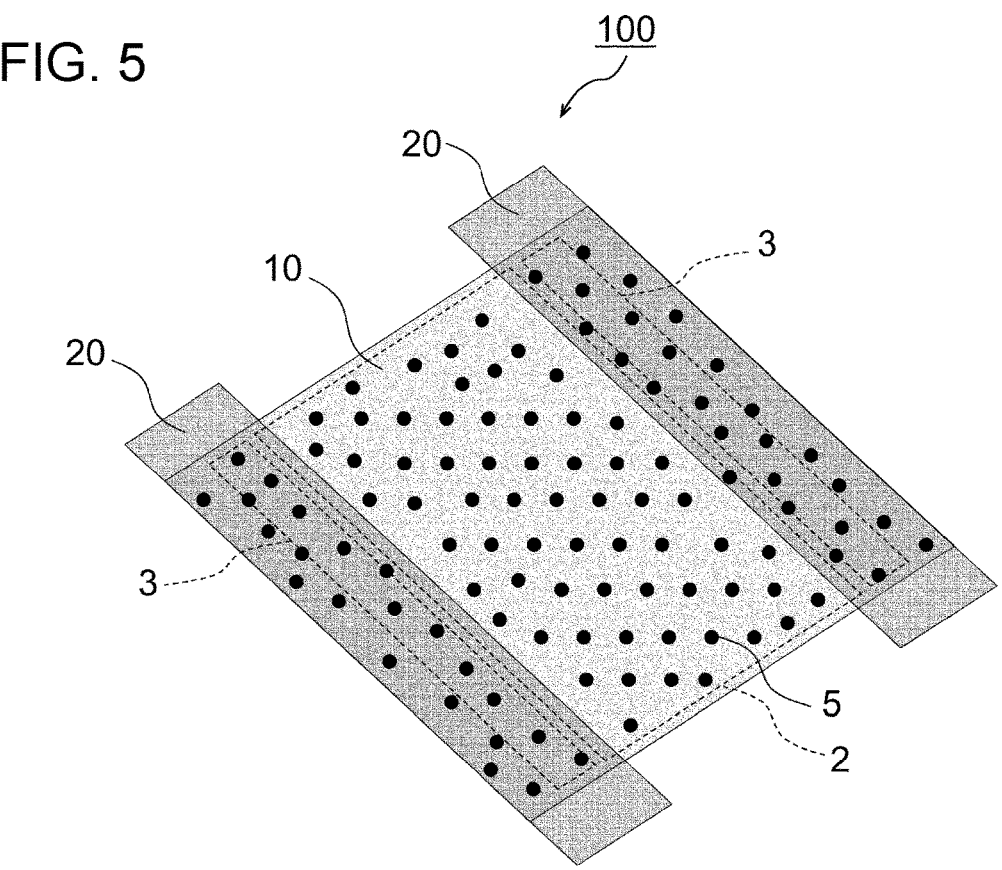
FIG. 5 is a perspective view of the chemical sensor according to the first embodiment after a magnetic-bead accumulation step.
Figure 6:
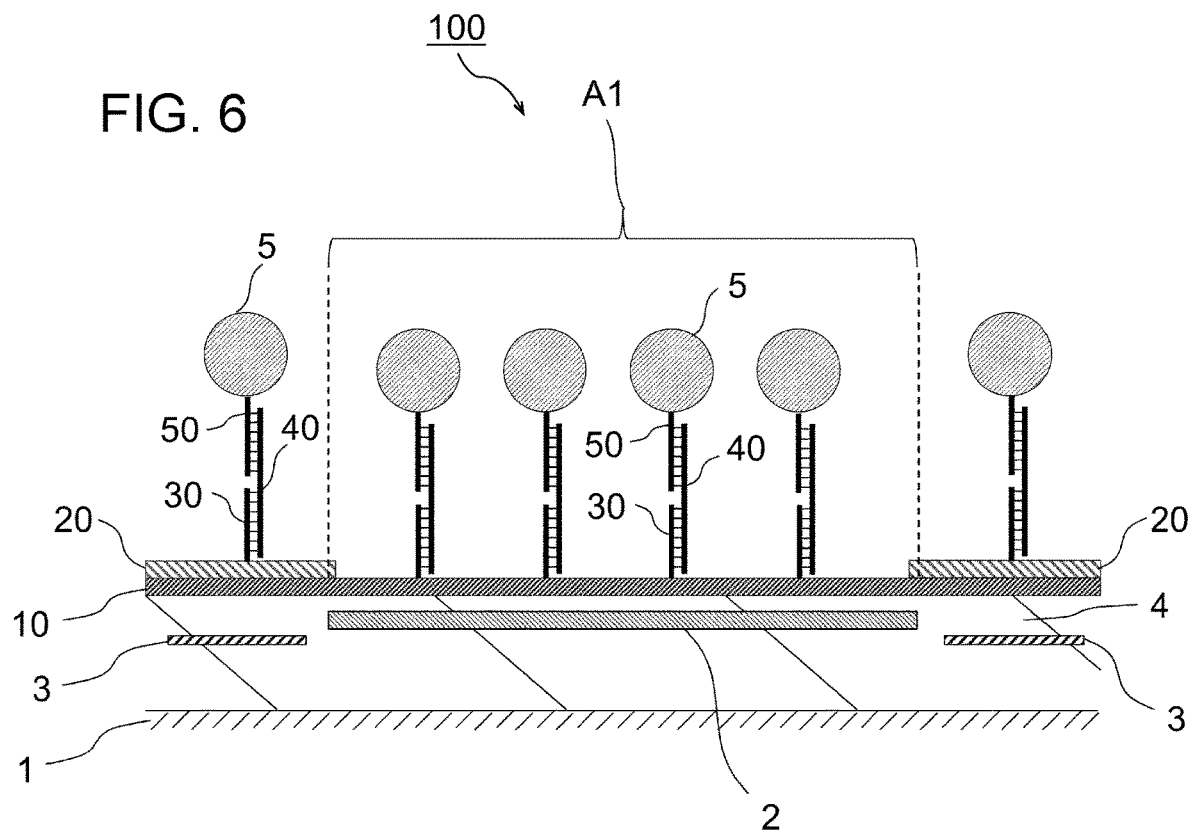
FIG. 6 is a sectional view of the chemical sensor according to the first embodiment after a magnetic-bead accumulation step.

The perspective view and the sectional view of the chemical sensor 100 after the magnetic-bead accumulation step are respectively provided in FIG. 5 and FIG. 6. In the magnetic-bead accumulation step, the labeling probe 50 on the surfaces of the magnetic beads 5 binds to the detection target substance 40 present over the first film 10 and the second films 20 to form complexes, so that the magnetic beads 5 are disposed over the first film 10 and the second films 20. The method of disposing the magnetic beads 5 over the first film 10 may be performed by applying any existing or future-developed technique, and may be any method as long as the magnetic beads 5 are measured to thereby indirectly detect the presence of the detection target substance.

(Dissolution Step)

The dissolution step is a step of bringing a dissolving liquid into contact with the first film 10 and the second films 20, to dissolve the second films 20. In the dissolution step, the dissolving liquid is passed through a microchannel, to thereby bring the dissolving liquid into contact with the first film 10 and the second films 20.

The dissolving liquid is, for example, an alkaline liquid or an acidic liquid. The alkaline liquid is, for example, an aqueous solution containing a base such as sodium hydroxide, potassium hydroxide, tris(hydroxymethyl)aminomethane, or ammonia. Such an alkaline dissolving liquid is preferably an aqueous solution of a strong base. The acidic liquid is, for example, an aqueous solution containing an acid such as hydrochloric acid, nitric acid, sulfuric acid, or phosphoric acid. Such an acidic dissolving liquid is preferably an aqueous solution of a strong acid. The formulation and pH of the dissolving liquid, the time for dissolution with the dissolving liquid, and the like are adjusted so as to maintain the binding between the first film 10 and the capture probe 30, the binding between the capture probe 30 and the detection target substance 40, and the binding between the detection target substance 40 and the labeling probe 50 (magnetic bead 5).

Figure 7:
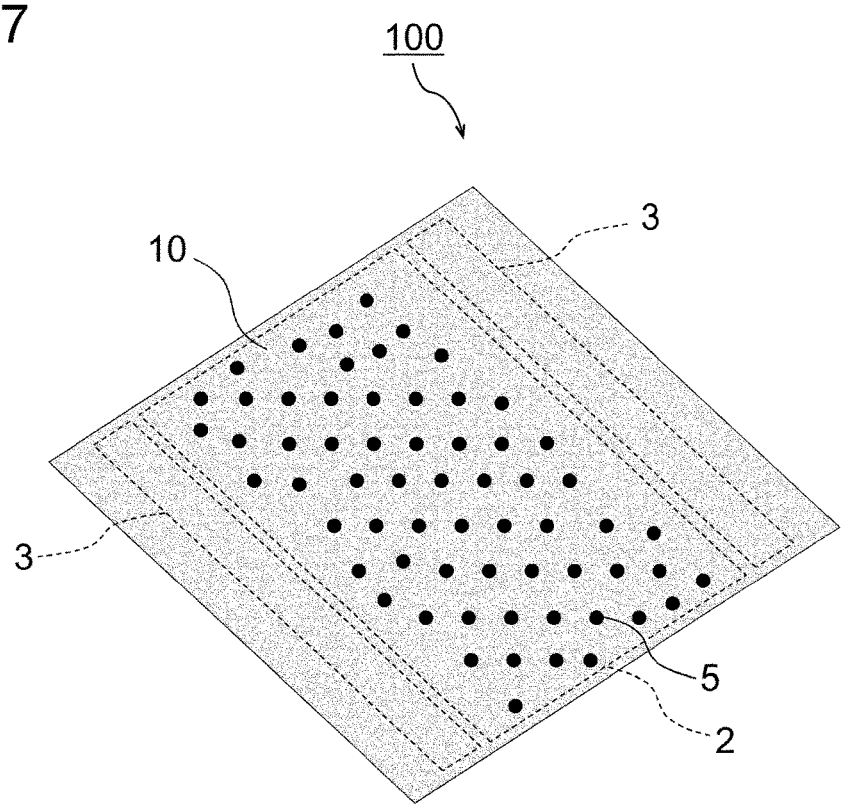
FIG. 7 is a perspective view of the chemical sensor according to the first embodiment after a dissolution step.
Figure 8:
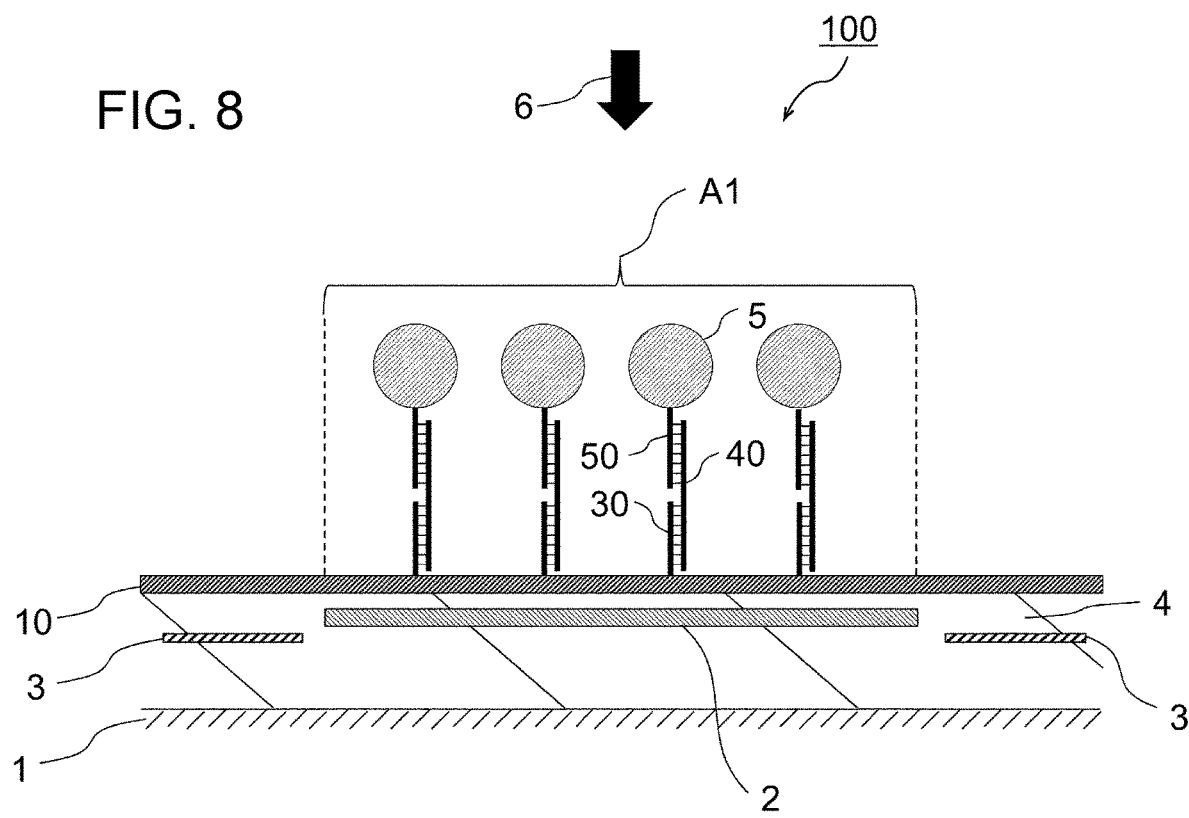
FIG. 8 is a sectional view of the chemical sensor according to the first embodiment after a dissolution step.

The perspective view and the sectional view of the chemical sensor 100 after the dissolution step are respectively provided in FIG. 7 and FIG. 8. In the dissolution step, the dissolving liquid is passed through a microchannel, to bring the dissolving liquid into contact with the first film 10 and the second films 20. As a result, the second films 20 are mainly dissolved, so that the magnetic beads 5 accumulated over the second films 20 and disposed over the magnetoresistance-effect elements 3 are removed over the magnetoresistance-effect elements 3. Since the first film 10 has low solubility in the dissolving liquid, the magnetic beads 5 disposed over the first film 10 are kept so as to be disposed over the first film 10, namely over the soft-magnetic-material film 2 (on the first region A1).

(Determination Step)

The determination step is a step of applying a magnetic field 6 to the chemical sensor 100 in a direction intersecting with the soft-magnetic-material film 2, to apply a detection magnetic field to the magnetoresistance-effect elements 3, and determining the resistance (or variation in the resistance) of the magnetoresistance-effect elements 3. The determination step will be described with an example in which, when viewed from a direction perpendicular to the film surface of the soft-magnetic-material film 2, the soft-magnetic-material film 2 and the magnetoresistance-effect elements 3 are disposed on the same straight line in the magnetization directions of the pinned layers of the magnetoresistance-effect elements 3, and, between the two magnetoresistance-effect elements 3, the pinned directions of the pinned layers are in the same direction. The magnetic field 6 applied in a direction intersecting with the film surface of the soft-magnetic-material film 2 is directed, by the soft-magnetic-material film 2, in the direction of the film surface of the soft-magnetic-material film 2, and applied, as a detection magnetic field, from the end surfaces of the soft-magnetic-material film 2 to the magnetoresistance-effect elements 3. After the dissolution step, the magnetic beads 5 binding to the detection target substance 40 are disposed over the soft-magnetic-material film 2 (on the first region A1); the larger the number of the magnetic beads 5 disposed on the first region A1, the higher the intensity of the detection magnetic field. In this example, between the two magnetoresistance-effect elements 3, the pinned directions of the pinned layers are in the same direction; the detection magnetic field is applied to the magnetoresistance-effect elements 3 in directions opposite to each other, so that the directions of variations in the resistances of the magnetoresistance-effect elements 3 in response to variation in the intensity of the detection magnetic field are opposite to each other. In this case, the two magnetoresistance-effect elements 3 are connected in series, and the differential voltage at the middle point of the connection of the two magnetoresistance-effect elements 3 is output, to thereby determine variations in the resistances of the two magnetoresistance-effect elements 3. In other words, since the voltage output from the middle point of the connection of the two magnetoresistance-effect elements 3 varies in response to the intensity of the detection magnetic field, this voltage output is determined to thereby detect the detection target substance 40. The number of the magnetic beads 5 disposed on the first region A1 correlates with the number of molecules of the detection target substance 40 present on the first region A1, and correlates with the number of molecules of the detection target substance 40 in the sample, so that the number of molecules of the detection target substance 40 in the sample can be determined.

Figure 14:
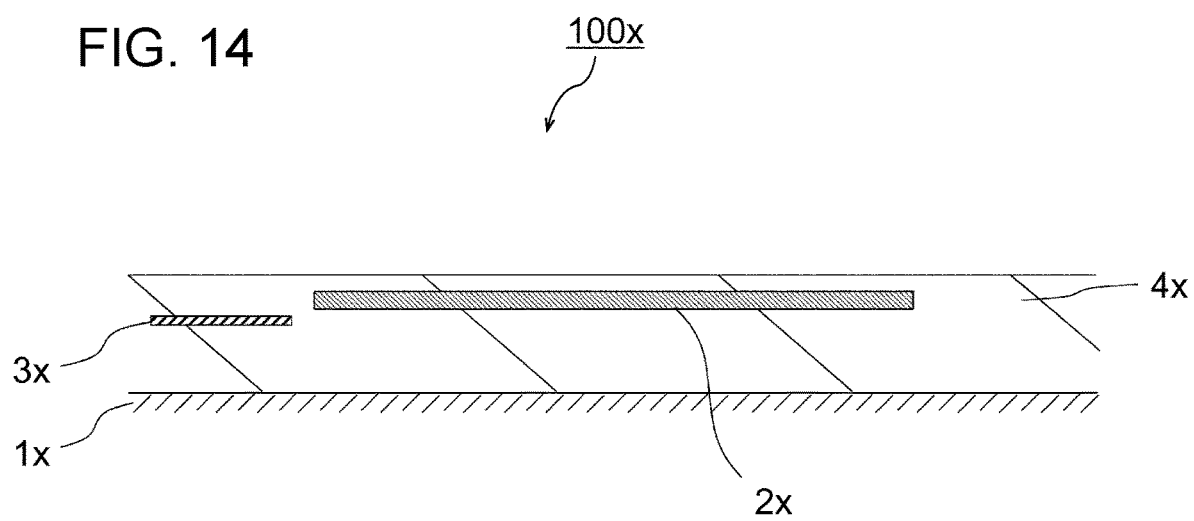
FIG. 14 is a sectional view of a biosensor described in the earlier application.

Here, the following case is considered: a single magnetic bead is disposed over the surface (on the protective film 4x) of the biosensor 100x illustrated in FIG. 14 and described in the earlier application. The resistance (or variation in the resistance) of the magnetoresistance-effect element 3x upon disposition of a single magnetic bead over the single magnetoresistance-effect element 3x is different from the resistance (or variation in the resistance) of the magnetoresistance-effect element 3x upon disposition of a single magnetic bead over the soft-magnetic-material thin film 2x. The probable reason for this is considered as follows. When a magnetic field is applied in a direction intersecting with the soft-magnetic-material thin film, a leakage magnetic field (stray magnetic field) is generated from the magnetic bead. The leakage magnetic field from the magnetic bead disposed over the magnetoresistance-effect element 3x is applied to the magnetoresistance-effect element 3x in a direction from the magnetoresistance-effect element 3x to the soft-magnetic-material thin film 2x. This direction of the leakage magnetic field is opposite to the direction of the detection magnetic field applied from the soft-magnetic-material thin film 2x to the magnetoresistance-effect element 3x. This probably results in the difference (the resistances vary in opposite directions) between the resistance (or variation in the resistance) of the magnetoresistance-effect element 3x due to the leakage magnetic field from the magnetic bead disposed over the soft-magnetic-material thin film 2x, and the resistance (or variation in the resistance) of the magnetoresistance-effect element 3x due to the leakage magnetic field from the magnetic bead disposed over the magnetoresistance-effect element 3x. As a result, when magnetic beads are disposed over the magnetoresistance-effect element 3x and over the soft-magnetic-material thin film 2x, in spite of the same number of magnetic beads disposed, the resistance of the magnetoresistance-effect element 3x varies depending on the arrangements of the magnetic beads. Thus, high detection accuracy is not provided. By contrast, in the chemical sensor 100 according to the first embodiment, the detection target substance 40 is detected while the magnetic beads 5 are disposed over the soft-magnetic-material film 2, but substantially not disposed over the magnetoresistance-effect elements 3. Thus, the chemical sensor 100 enables high detection accuracy.

As has been described, the chemical sensor 100 includes the soft-magnetic-material film 2, the magnetoresistance-effect element 3, the first film 10 disposed over the soft-magnetic-material film 2, and the second film 20 disposed over the magnetoresistance-effect element 3, wherein, when viewed from a direction perpendicular to the film surface of the soft-magnetic-material film 2, the soft-magnetic-material film 2 is disposed at least partially so as not to overlap the magnetoresistance-effect element 3; when viewed from the direction perpendicular to the film surface of the soft-magnetic-material film 2, the magnetoresistance-effect element 3 is disposed at least partially so as not to overlap the soft-magnetic-material film 2; and the second film 20 has higher solubility in a specific liquid (dissolving liquid) than the first film 10.

Thus, in the chemical sensor 100, a liquid (dissolving liquid) in which the second film 20 has higher solubility than the first film 10 is brought into contact with the first film and the second film, to thereby mainly dissolve the second film. Upon disposition of the magnetic beads 5 on the first region A1 of the first film 10, even when the magnetic beads 5 are disposed over the second film 20, namely over the magnetoresistance-effect element 3, the second film 20 is mainly dissolved, so that, while the magnetic beads 5 disposed on the first region A1 are kept, the magnetic beads 5 disposed over the second film 20, namely over the magnetoresistance-effect element 3, are removed. In this way, the detection target substance 40 is detected while the magnetic beads 5 are disposed over the soft-magnetic-material film 2, but substantially not disposed over the magnetoresistance-effect element 3. Therefore, the chemical sensor 100 enables high detection accuracy.

Another chemical sensor 100 includes the soft-magnetic-material film 2, the magnetoresistance-effect element 3, the first film 10 disposed over the soft-magnetic-material film 2, and the second film 20 disposed over the magnetoresistance-effect element 3, wherein, when viewed from a direction perpendicular to the film surface of the soft-magnetic-material film 2, the soft-magnetic-material film 2 is disposed at least partially so as not to overlap the magnetoresistance-effect element 3; when viewed from the direction perpendicular to the film surface of the soft-magnetic-material film 2, the magnetoresistance-effect element 3 is disposed at least partially so as not to overlap the soft-magnetic-material film 2; the material of the first film 10 is at least one selected from the group consisting of silicon, titanium, zirconium, indium, tantalum, iron, cobalt, nickel, copper, cadmium, bismuth, gold, silver, rhodium, ruthenium, palladium, and alloys of combinations thereof, an oxide of at least one selected from the group consisting of silicon, titanium, zirconium, indium, tantalum, iron, cobalt, nickel, copper, cadmium, bismuth, and combinations thereof, or at least one selected from the group consisting of carbon, diamond-like carbon, and resin; and the material of the second film 20 is at least one selected from the group consisting of aluminum, zinc, gallium, tin, lead, niobium, molybdenum, tungsten, and alloys of combinations thereof, or an oxide of at least one selected from the group consisting of aluminum, zinc, gallium, tin, lead, niobium, molybdenum, tungsten, and combinations thereof.

Thus, in the chemical sensor 100, the material of the first film 10 is less soluble, but the material of the second film 20 is more soluble in an alkaline liquid; the alkaline liquid is then brought into contact with the first film 10 and the second film 20, to thereby mainly dissolve the second film. During disposition of the magnetic beads 5 on the first region A1 of the first film 10, even when the magnetic beads 5 are disposed over the second film 20, namely over the magnetoresistance-effect element 3, the second film 20 is mainly dissolved, so that, while the magnetic beads 5 disposed on the first region A1 are kept, the magnetic beads 5 disposed over the second film 20, namely over the magnetoresistance-effect element 3, are removed. In this way, the detection target substance 40 is detected while the magnetic beads 5 are disposed over the soft-magnetic-material film 2, but substantially not disposed over the magnetoresistance-effect element 3. Therefore, the chemical sensor 100 enables high detection accuracy.

Another chemical sensor 100 includes the soft-magnetic-material film 2, the magnetoresistance-effect element 3, the first film 10 disposed over the soft-magnetic-material film 2, and the second film 20 disposed over the magnetoresistance-effect element 3, wherein, when viewed from a direction perpendicular to the film surface of the soft-magnetic-material film 2, the soft-magnetic-material film 2 is disposed at least partially so as not to overlap the magnetoresistance-effect element 3; when viewed from the direction perpendicular to the film surface of the soft-magnetic-material film 2, the magnetoresistance-effect element 3 is disposed at least partially so as not to overlap the soft-magnetic-material film 2; the material of the first film 10 is at least one selected from the group consisting of silicon, titanium, zirconium, indium, tantalum, niobium, molybdenum, tungsten, gold, silver, rhodium, ruthenium, palladium, and alloys of combinations thereof, an oxide of at least one selected from the group consisting of silicon, titanium, zirconium, indium, tantalum, niobium, molybdenum, tungsten, and combinations thereof, or at least one selected from the group consisting of carbon, diamond-like carbon, and resin; and the material of the second film 20 is at least one selected from the group consisting of aluminum, zinc, gallium, tin, lead, iron, cobalt, nickel, copper, cadmium, bismuth, and alloys of combinations thereof, or an oxide of at least one selected from the group consisting of aluminum, zinc, gallium, tin, lead, iron, cobalt, nickel, copper, cadmium, bismuth, and combinations thereof.

Thus, in the chemical sensor 100, the material of the first film 10 is less soluble, but the material of the second film 20 is more soluble in an acidic liquid; the acidic liquid is then brought into contact with the first film 10 and the second film 20, to thereby mainly dissolve the second film. During disposition of the magnetic beads 5 on the first region A1 of the first film 10, even when the magnetic beads 5 are disposed over the second film 20, namely over the magnetoresistance-effect element 3, the second film 20 is mainly dissolved, so that, while the magnetic beads 5 disposed on the first region A1 are kept, the magnetic beads 5 disposed over the second film 20, namely over the magnetoresistance-effect element 3, are removed. In this way, the detection target substance 40 is detected while the magnetic beads 5 are disposed over the soft-magnetic-material film 2, but substantially not disposed over the magnetoresistance-effect element 3. Therefore, the chemical sensor 100 enables high detection accuracy.

The second film 20 is preferably disposed over the whole region facing the magnetoresistance-effect element 3, more preferably, as illustrated in FIG. 2, disposed over a region wider than the region facing the magnetoresistance-effect element 3. As illustrated in FIG. 2, in the chemical sensor 100, such second films 20 are disposed also over the magnetoresistance-effect element 3-side end portions of the soft-magnetic-material film 2. In this case, the detection target substance 40 is detected while the magnetic beads 5 are not disposed near the magnetoresistance-effect elements 3. Therefore, the chemical sensor 100 enables higher detection accuracy.

Figure 9:
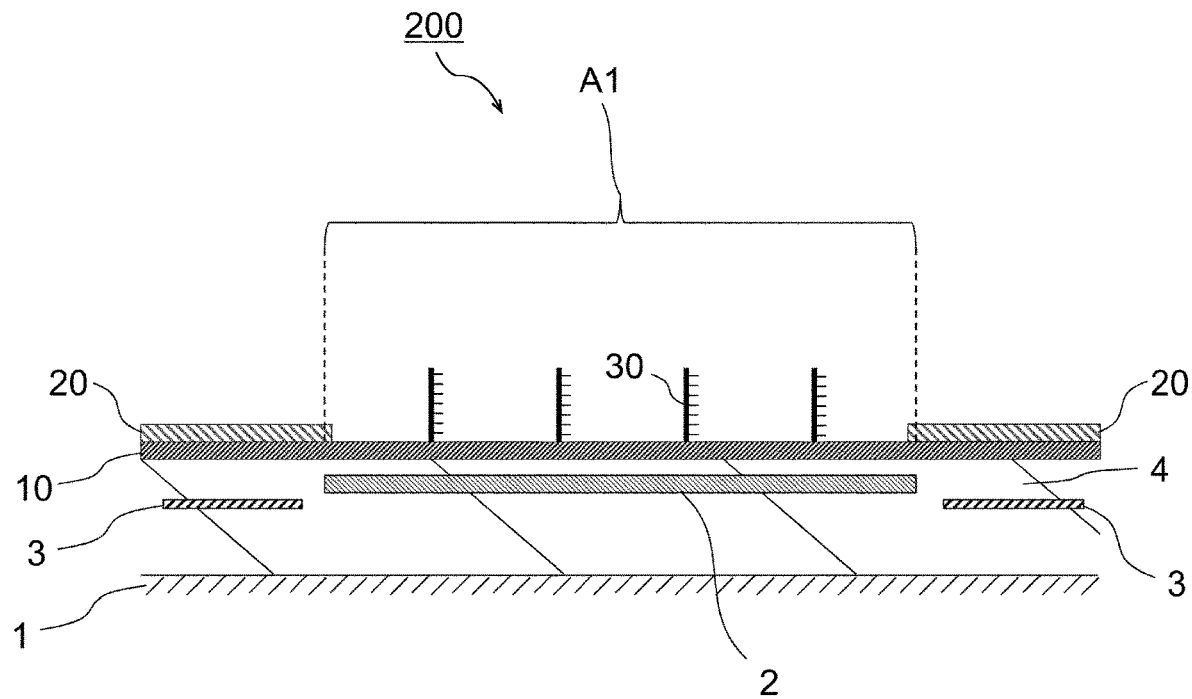
FIG. 9 is a sectional view of a chemical sensor according to a second embodiment.

Such a preferred embodiment according to the present disclosure has been described so far. However, the chemical sensor according to the above-described embodiment of the present disclosure can be modified. For example, the first embodiment is described above with the example in which the capture probe 30 is immobilized on the first film 10 and on the second films 20. Alternatively, as illustrated in FIG. 9, a chemical sensor 200 according to a second embodiment may be provided in which the capture probe 30 is not immobilized on the second films 20. Such an embodiment can be provided, for example, in the following manner: the material of the first film 10 is selected to be a metal such as gold or silver; the material of the second films 20 is selected to be an oxide such as aluminum oxide or zinc oxide; and the linker is selected to be a thiolic acid derivative. Such materials are employed, so that the linker binds to the surface of the first film 10, but does not bind to the surfaces of the second films 20. In this case, the capture probe 30 is immobilized on the first film 10 to which the linker is binding, and is not immobilized on the second films 20 free from the linker. In the chemical sensor 200, even when the magnetic-bead accumulation step causes the magnetic beads 5 to be disposed over the second films 20 (over the magnetoresistance-effect elements 3), as in the chemical sensor 100, the dissolution step is performed to mainly dissolve the second films 20, compared with the first film 10. Therefore, the detection target substance 40 is detected while the magnetic beads 5 are disposed over the soft-magnetic-material film 2, but substantially not disposed over the magnetoresistance-effect element 3.

The first embodiment is described above with the example in which the two magnetoresistance-effect elements 3 are disposed on both sides of the soft-magnetic-material film 2 in a direction parallel to the film surface of the soft-magnetic-material film 2. Alternatively, only a single magnetoresistance-effect element 3 may be provided. In this case, the detection target substance 40 is also detected by determining the resistance (or variation in the resistance) of the magnetoresistance-effect element 3.

The first embodiment is described above with the example in which the first film 10 and the protective film 4 are different elements. Alternatively, the first film 10 may be provided so as to function also as the protective film 4. In this case, the material of the first film 10 is preferably an insulator.

Figure 10:
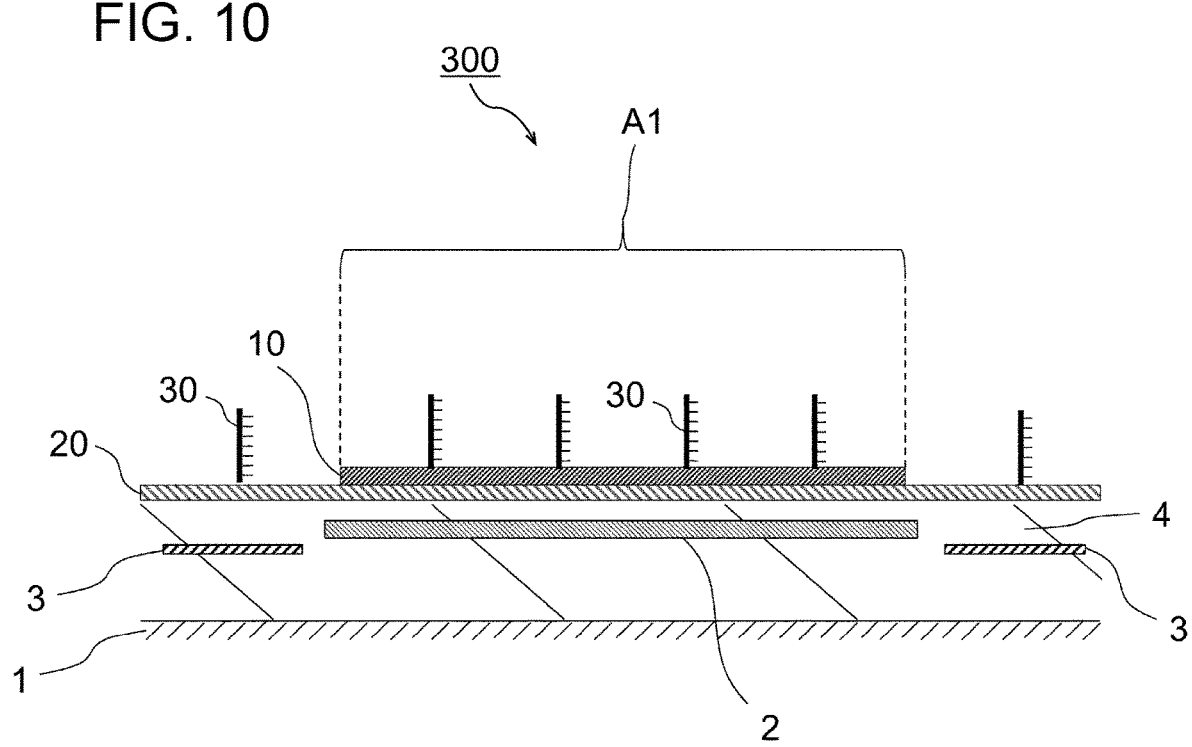
FIG. 10 is a sectional view of a chemical sensor according to a third embodiment.
Figure 11:
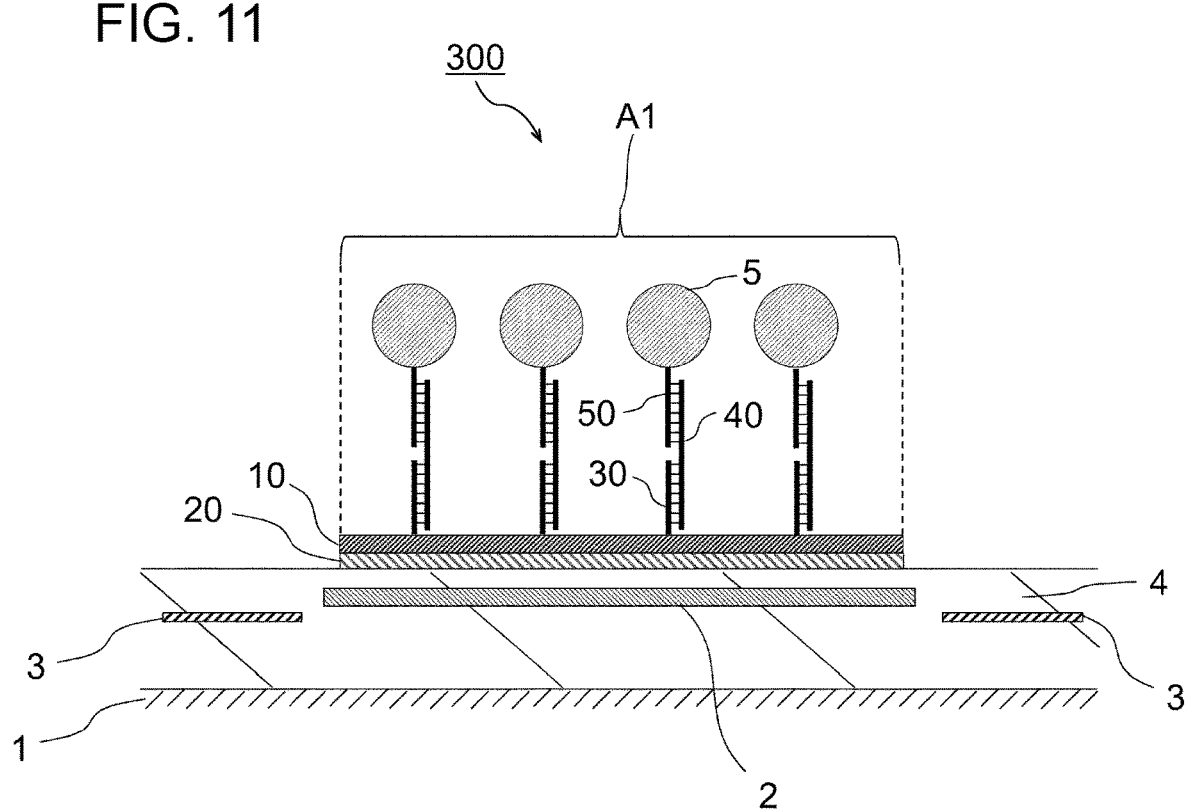
FIG. 11 is a sectional view of the chemical sensor according to the third embodiment after a dissolution step.

The first embodiment is described above with the example in which the first film 10 is disposed over the soft-magnetic-material film 2 and the magnetoresistance-effect element 3, and the second films 20 are disposed on the first film 10. Alternatively, as illustrated in FIG. 10, a chemical sensor 300 according to a third embodiment may be provided in which the second film 20 is disposed over the soft-magnetic-material film 2 and the magnetoresistance-effect elements 3, and the first film 10 is disposed on the second film 20. In this case, in order to achieve a state illustrated in FIG. 11 at the time of completion of the dissolution step, the formulation and pH of the dissolving liquid, the time for dissolution with the dissolving liquid, and the like are adjusted.

As illustrated in FIG. 10, in the chemical sensor 300, the first film 10 is preferably not disposed over the magnetoresistance-effect element 3-side end portions of the soft-magnetic-material film 2. In this case, the detection target substance 40 is detected while the magnetic beads 5 are not disposed over portions of the soft-magnetic-material film 2, the portions being near the magnetoresistance-effect elements 3. Therefore, the chemical sensor 300 enables higher detection accuracy.

Figure 12:
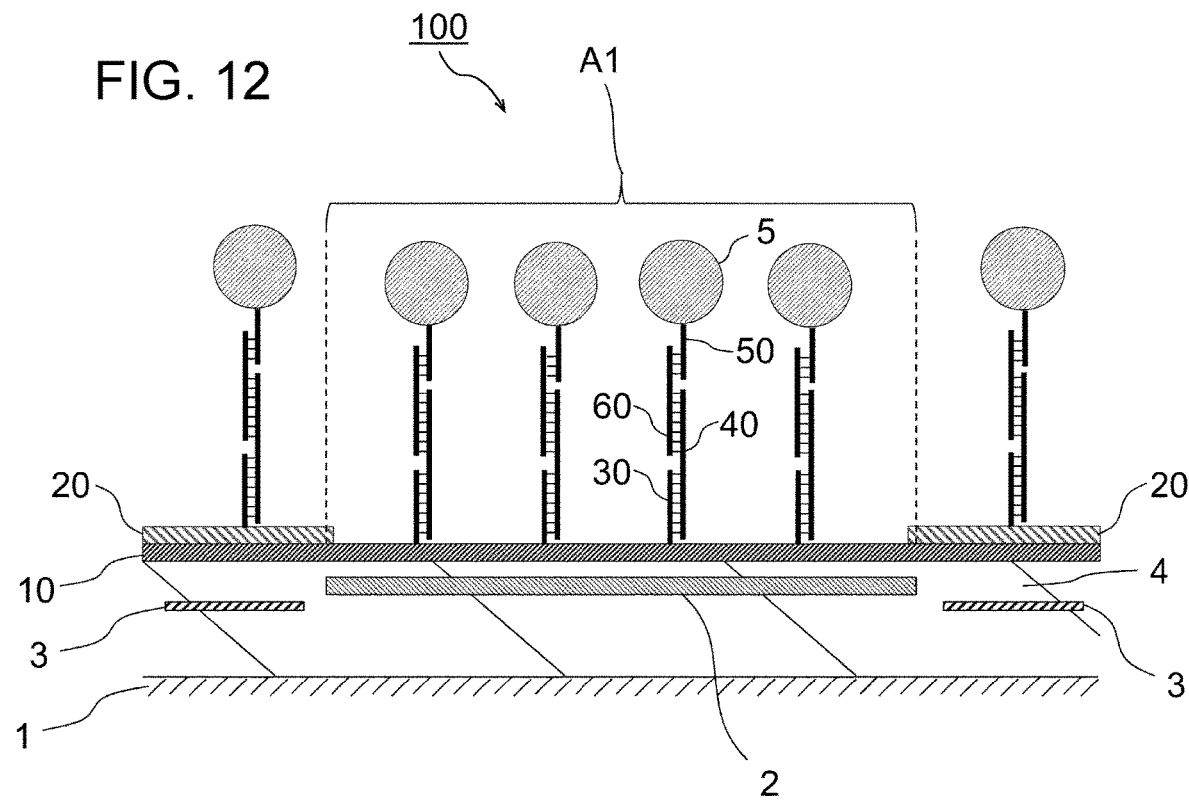
FIG. 12 is a sectional view of a chemical sensor according to another example of the first embodiment after a magnetic-bead accumulation step.
Figure 13:
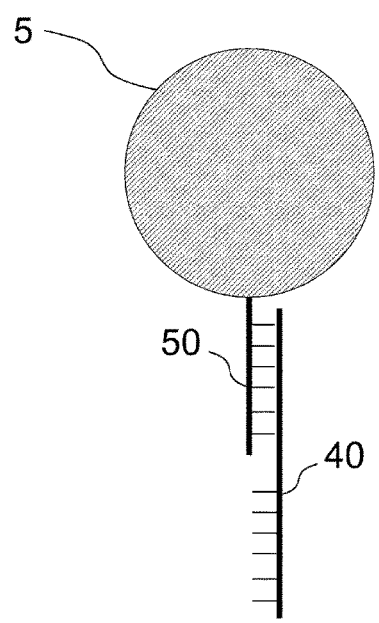
FIG. 13 is a schematic sectional view of a magnetic bead to which a detection target substance is binding.

The first embodiment is described above with the example in which the magnetic bead 5 having the labeling probe 50 directly binds to the detection target substance 40. Alternatively, the magnetic bead 5 may bind to the detection target substance 40 via a probe 60 that binds to the detection target substance 40 and the magnetic bead 5 (labeling probe 50). In this case, a probe binding step of causing the probe 60 to bind to the detection target substance 40 binding to the capture probe 30, is performed between the detection-target-substance accumulation step and the magnetic-bead accumulation step. FIG. 12 is a sectional view of the chemical sensor 100 after the magnetic-bead accumulation step when the probe binding step is additionally performed between the detection-target-substance accumulation step and the magnetic-bead accumulation step. The probe 60 is, for example, as follows: when the detection target substance 40 and the labeling probe 50 are both nucleic acids, the probe 60 may be a nucleic acid complementary to these two nucleic acids; when the detection target substance 40 is an antigen and the labeling probe 50 is a secondary antibody, the probe 60 may be a primary antibody that binds to the antigen and the secondary antibody; when the detection target substance 40 is a nucleic acid and the labeling probe 50 is streptavidin, the probe 60 may be a biotin-terminated nucleic acid complementary to the nucleic acid. The probe 60 preferably has a site that binds to the detection target substance 40, and another site that binds to the labeling probe 50.

The first embodiment is described above with the example in which the detection target substance 40 is caused to bind to the capture probe 30, and subsequently the magnetic beads 5 (labeling probe 50) are caused to bind to the detection target substance 40. However, as long as a step of measuring the magnetic beads 5 to indirectly detect the presence of the detection target substance 40 is provided, the order of performing the following may be changed: formation of the binding between the capture probe 30 and the detection target substance 40, formation of the binding between the detection target substance 40 and the magnetic beads 5, formation of the binding between the detection target substance 40 and the probe 60, and formation of the binding between the probe 60 and the magnetic beads 5. For example, a sample and a dispersion liquid of the magnetic beads 5 are mixed together to cause binding between the detection target substance 40 and the magnetic beads 5 (labeling probe 50), to form complexes of the detection target substance 40 and the labeling probe 50. Subsequently, the magnetic beads 5 binding to the detection target substance 40 are isolated with a magnet, rinsed with a buffer or the like, and dispersed again to obtain a dispersion liquid of the magnetic beads 5 (illustrated in FIG. 13) to the surfaces of which the detection target substance 40 binds via the labeling probe 50. Furthermore, the dispersion liquid of the magnetic beads 5 binding to the detection target substance 40 is brought into contact with the first film 10 and the second film 20 of the chemical sensor 100, to thereby achieve binding between the capture probe 30 and the detection target substance 40 binding to the magnetic beads 5. In this case, measurement of the magnetic beads 5 also enables indirect detection of the presence of the detection target substance 40. Alternatively, as long as a step of measuring the magnetic beads 5 to indirectly detect the presence of the detection target substance is provided, two or more of the following bindings may be simultaneously formed in a single step: the binding between the capture probe 30 and the detection target substance 40, the binding between the detection target substance 40 and the magnetic beads 5, binding between the detection target substance 40 and the probe 60, and the binding between the probe 60 and the magnetic beads 5.

REFERENCE SIGNS LIST

1 substrate
2 soft-magnetic-material film
3 magnetoresistance-effect element
4 protective film
5 magnetic bead
6 magnetic field
10 first film
20 second film
30 capture probe
40 detection target substance
50 labeling probe
60 probe
100, 200, 300 chemical sensors

The invention claimed is:

1. A chemical sensor comprising:
   a soft-magnetic-material film;
   a magnetoresistance-effect element;
   a first film disposed over the soft-magnetic-material film; and
   a second film disposed over the magnetoresistance-effect element,
   wherein, when viewed from a direction perpendicular to a film surface of the soft-magnetic-material film, the soft-magnetic-material film is disposed at least partially so as not to overlap the magnetoresistance-effect element,
   when viewed from the direction perpendicular to the film surface of the soft-magnetic-material film, the magnetoresistance-effect element is disposed at least partially so as not to overlap the soft-magnetic-material film, and
   the second film has higher solubility in a specific liquid than the first film.

2. The chemical sensor according to claim 1, wherein the first film is disposed over the soft-magnetic-material film and the magnetoresistance-effect element, and the second film is disposed over the first film.

3. The chemical sensor according to claim 1, wherein the specific liquid is an alkaline liquid.

4. The chemical sensor according to claim 1, wherein the specific liquid is an acidic liquid.

5. The chemical sensor according to claim 1, wherein a material of the first film is at least one selected from the group consisting of carbon, diamond-like carbon, and resin.

6. The chemical sensor according to claim 5, wherein a material of the second film is at least one selected from the group consisting of aluminum, zinc, gallium, tin, lead, niobium, molybdenum, tungsten, and alloys of combinations thereof.

7. The chemical sensor according to claim 5, wherein a material of the second film is an oxide of at least one selected from the group consisting of aluminum, zinc, gallium, tin, lead, niobium, molybdenum, tungsten, and combinations thereof.

8. The chemical sensor according to claim 5, wherein a material of the second film is at least one selected from the group consisting of aluminum, zinc, gallium, tin, lead, iron, cobalt, nickel, copper, cadmium, bismuth, and alloys of combinations thereof.

9. The chemical sensor according to claim 5, wherein a material of the second film is an oxide of at least one selected from the group consisting of aluminum, zinc, gallium, tin, lead, iron, cobalt, nickel, copper, cadmium, bismuth, and combinations thereof.

10. The chemical sensor according to claim 3, wherein a material of the first film is at least one selected from the group consisting of silicon, titanium, zirconium, indium, tantalum, iron, cobalt, nickel, copper, cadmium, bismuth, gold, silver, rhodium, ruthenium, palladium, and alloys of combinations thereof.

11. The chemical sensor according to claim 3, wherein a material of the first film is an oxide of at least one selected from the group consisting of silicon, titanium, zirconium, indium, tantalum, iron, cobalt, nickel, copper, cadmium, bismuth, and combinations thereof.

12. The chemical sensor according to claim 4, wherein a material of the first film is at least one selected from the group consisting of silicon, titanium, zirconium, indium, tantalum, niobium, molybdenum, tungsten, gold, silver, rhodium, ruthenium, palladium, and alloys of combinations thereof.

13. The chemical sensor according to claim 4, wherein a material of the first film is an oxide of at least one selected from the group consisting of silicon, titanium, zirconium, indium, tantalum, niobium, molybdenum, tungsten, and combinations thereof.

14. The chemical sensor according to claim 3, wherein a material of the second film is at least one selected from the group consisting of aluminum, zinc, gallium, tin, lead, niobium, molybdenum, tungsten, and alloys of combinations thereof.

15. The chemical sensor according to claim 3, wherein a material of the second film is an oxide of at least one selected from the group consisting of aluminum, zinc, gallium, tin, lead, niobium, molybdenum, tungsten, and combinations thereof.

16. The chemical sensor according to claim 4, wherein a material of the second film is at least one selected from the group consisting of aluminum, zinc, gallium, tin, lead, iron, cobalt, nickel, copper, cadmium, bismuth, and alloys of combinations thereof.

17. The chemical sensor according to claim 4, wherein a material of the second film is an oxide of at least one selected from the group consisting of aluminum, zinc, gallium, tin, lead, iron, cobalt, nickel, copper, cadmium, bismuth, and combinations thereof.

18. A chemical sensor comprising:
a soft-magnetic-material film;
a magnetoresistance-effect element;
a first film disposed over the soft-magnetic-material film; and
a second film disposed over the magnetoresistance-effect element,
wherein, when viewed from a direction perpendicular to a film surface of the soft-magnetic-material film, the soft-magnetic-material film is disposed at least partially so as not to overlap the magnetoresistance-effect element,
when viewed from the direction perpendicular to the film surface of the soft-magnetic-material film, the magnetoresistance-effect element is disposed at least partially so as not to overlap the soft-magnetic-material film,
a material of the first film is at least one selected from the group consisting of silicon, titanium, zirconium, indium, tantalum, iron, cobalt, nickel, copper, cadmium, bismuth, gold, silver, rhodium, ruthenium, palladium, and alloys of combinations thereof, or
an oxide of at least one selected from the group consisting of silicon, titanium, zirconium, indium, tantalum, iron, cobalt, nickel, copper, cadmium, bismuth, and combinations thereof, or
at least one selected from the group consisting of carbon, diamond-like carbon, and resin, and
a material of the second film is at least one selected from the group consisting of aluminum, zinc, gallium, tin, lead, niobium, molybdenum, tungsten, and alloys of combinations thereof, or
an oxide of at least one selected from the group consisting of aluminum, zinc, gallium, tin, lead, niobium, molybdenum, tungsten, and combinations thereof.

19. A chemical sensor comprising:
a soft-magnetic-material film;
a magnetoresistance-effect element;
a first film disposed over the soft-magnetic-material film; and
a second film disposed over the magnetoresistance-effect element,
wherein, when viewed from a direction perpendicular to a film surface of the soft-magnetic-material film, the soft-magnetic-material film is disposed at least partially so as not to overlap the magnetoresistance-effect element,
when viewed from the direction perpendicular to the film surface of the soft-magnetic-material film, the magnetoresistance-effect element is disposed at least partially so as not to overlap the soft-magnetic-material film,
a material of the first film is at least one selected from the group consisting of silicon, titanium, zirconium, indium, tantalum, niobium, molybdenum, tungsten, gold, silver, rhodium, ruthenium, palladium, and alloys of combinations thereof, or
an oxide of at least one selected from the group consisting of silicon, titanium, zirconium, indium, tantalum, niobium, molybdenum, tungsten, and combinations thereof, or
at least one selected from the group consisting of carbon, diamond-like carbon, and resin, and
a material of the second film is at least one selected from the group consisting of aluminum, zinc, gallium, tin, lead, iron, cobalt, nickel, copper, cadmium, bismuth, and alloys of combinations thereof, or
an oxide of at least one selected from the group consisting of aluminum, zinc, gallium, tin, lead, iron, cobalt, nickel, copper, cadmium, bismuth, and combinations thereof.

* * * * *